United States Patent
Savage et al.

(10) Patent No.: US 9,138,595 B2
(45) Date of Patent: Sep. 22, 2015

(54) HAND-HELD PROGRAMMABLE OCULAR LIGHT THERAPY APPARATUS AND METHODS

(75) Inventors: Kent W. Savage, American Fork, UT (US); Steven D. Powell, Orem, UT (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1680 days.

(21) Appl. No.: 11/170,914

(22) Filed: Jun. 30, 2005

(65) Prior Publication Data
US 2006/0009822 A1    Jan. 12, 2006

Related U.S. Application Data

(63) Continuation-in-part of application No. 10/692,893, filed on Oct. 24, 2003.

(60) Provisional application No. 60/476,574, filed on Jun. 6, 2003.

(51) Int. Cl.
*A61N 5/06* (2006.01)
*A61M 21/00* (2006.01)

(52) U.S. Cl.
CPC ............. *A61N 5/0618* (2013.01); *A61M 21/00* (2013.01); *A61M 2021/0044* (2013.01);
(Continued)

(58) Field of Classification Search
CPC ............. A61N 2005/0652; A61N 2005/0627; A61N 2005/0062; A61N 5/0616; A61B 2017/00057; A61B 1/0684
USPC ..................................... 606/2–19; 607/88–94
See application file for complete search history.

(56) References Cited

U.S. PATENT DOCUMENTS 4,940,323 A    7/1990  Downing
5,197,941 A *  3/1993  Whitaker ........................ 600/27
(Continued)

FOREIGN PATENT DOCUMENTS

EP    1134491 A2    8/2001
EP    1285676 A2    8/2002
(Continued)

OTHER PUBLICATIONS

Chen, "A Cold Cathode Fluorescent Lamp (CCFL) Controller Used in Magnetic Transformer Application," <<http://www.chipcenter.com/analog/c070.htm>>, accessed Jun. 6, 2003.
(Continued)

*Primary Examiner* — Aaron Roane

(57) ABSTRACT

In one of many possible embodiments, a light therapy apparatus is provided for delivering ocular light to a subject to treat a disorder that is responsive to ocular light therapy. The apparatus comprises a power supply, a hand-held light output device having light sources powered by the power supply, and a programmable data processor coupled to the power supply and the light output device. The programmable data processor is configured to control light emissions from the hand-held light output device. In some embodiments, the plurality of light sources may provide a light output having at least forty percent blue light with a wavelength range of approximately 435 nm to 500 nm. In some embodiments, the programmable data processor is configured to control light emissions in accordance with user-defined light therapy programs.

27 Claims, 8 Drawing Sheets

(52) U.S. Cl.
CPC . *A61M 2205/8206* (2013.01); *A61M 2209/084* (2013.01); *A61N 5/0616* (2013.01); *A61N 2005/0627* (2013.01); *A61N 2005/0644* (2013.01); *A61N 2005/0652* (2013.01); *A61N 2005/0655* (2013.01)

(56) References Cited

U.S. PATENT DOCUMENTS

| | | | |
|---|---|---|---|
| 5,304,212 A | | 4/1994 | Czeisler et al. |
| 5,447,527 A | * | 9/1995 | Waldman ............ 607/88 |
| 5,447,528 A | | 9/1995 | Geraldo |
| 5,467,258 A | | 11/1995 | Bamber et al. |
| 5,503,637 A | | 4/1996 | Kyricos |
| 5,589,741 A | | 12/1996 | Terman et al. |
| 5,800,479 A | * | 9/1998 | Thiberg ............ 607/88 |
| 6,024,760 A | * | 2/2000 | Marchesi ............ 607/96 |
| 6,053,936 A | | 4/2000 | Koyoma et al. |
| 6,056,936 A | * | 5/2000 | Nougayrede et al. ...... 423/574.1 |
| 6,063,108 A | * | 5/2000 | Salansky et al. ............ 607/89 |
| 6,135,117 A | | 10/2000 | Campbell et al. |
| 6,135,620 A | | 10/2000 | Marsh |
| 6,350,275 B1 | | 2/2002 | Vreman et al. |
| 6,381,124 B1 | | 4/2002 | Whitcher et al. |
| 6,454,789 B1 | | 9/2002 | Chen |
| 6,488,698 B1 | | 12/2002 | Hyman |
| 6,493,217 B1 | * | 12/2002 | Jenkins, Jr. ............ 361/679.6 |
| 6,596,571 B2 | | 7/2003 | Arao et al. |
| 6,602,275 B1 | * | 8/2003 | Sullivan ............ 607/88 |
| 6,612,713 B1 | | 9/2003 | Kuelbs |
| 6,831,689 B2 | | 12/2004 | Yadid-Pecht |
| 6,875,225 B1 | | 4/2005 | Pederson |
| 7,057,886 B2 | | 6/2006 | Yano et al. |
| 2001/0056293 A1 | | 12/2001 | Brainard |
| 2002/0010500 A1 | * | 1/2002 | Chen ............ 607/89 |
| 2002/0029071 A1 | * | 3/2002 | Whitehurst ............ 607/88 |
| 2002/0048169 A1 | * | 4/2002 | Dowling et al. ............ 362/234 |
| 2002/0198576 A1 | * | 12/2002 | Chen et al. ............ 607/88 |
| 2003/0023283 A1 | * | 1/2003 | McDaniel ............ 607/88 |
| 2003/0072156 A1 | * | 4/2003 | Pohlert et al. ............ 362/244 |
| 2003/0109860 A1 | * | 6/2003 | Black ............ 606/10 |
| 2003/0233138 A1 | * | 12/2003 | Spooner ............ 607/93 |
| 2004/0120152 A1 | * | 6/2004 | Bolta et al. ............ 362/294 |

FOREIGN PATENT DOCUMENTS

| | | |
|---|---|---|
| JP | 01-503607 B1 | 7/1990 |
| JP | 02-302276 A1 | 12/1990 |
| JP | 04-506020 B1 | 10/1992 |
| JP | 08-150210 A1 | 6/1996 |
| JP | 09-213101 A1 | 8/1997 |
| JP | 2000279522 A | 10/2000 |
| WO | 8908475 A1 | 9/1989 |
| WO | 03040808 A2 | 5/2003 |

OTHER PUBLICATIONS

HP Jornada 700 Series Handheld PC User's Guide; pp. 129, 136; 2001.

* cited by examiner

HAND-HELD PROGRAMMABLE OCULAR LIGHT THERAPY APPARATUS AND METHODS

RELATED APPLICATIONS

This application is a continuation in part of U.S. patent application Ser. No. 10/692,893, entitled HAND-HELD LIGHT THERAPY APPARATUS AND METHOD, filed Oct. 24, 2003, which application claims priority under 35 U.S.C. §119(e) to U.S. Provisional Patent Application No. 60/476,574, filed Jun. 6, 2003. The present application is related to PCT application number PCT/US04/017683, filed Jun. 4, 2004. The contents of the foregoing applications are hereby incorporated by reference in their entireties.

FIELD

This application relates to light therapy apparatus and methods. More particularly, this application concerns programmable apparatus and methods for delivering light to a subject's eyes to provide circadian rhythm adjustments or to treat jet lag, seasonal affective disorder, mood and sleep disorders, and other disorders or problems may be treated with light therapy.

BACKGROUND

Ocular light therapy systems have been widely used for some time to treat circadian rhythm disorders, seasonal affective disorder and other such problems by delivering light through the eyes of a subject. One problem has been the need to provide the necessary light intensity and color spectrum, similar to daylight. In many cases, fluorescent lights are used because they tend to provide an effective spectrum of light and are longer lasting than incandescent lamps. However, the high intensities of light needed for such treatments required relatively large-sized lamps and other components. Thus, many commercial light therapy units have been large, bulky and cumbersome.

In the last decade, advances in ballast and fluorescent light technology have allowed some companies to produce smaller, lighter-weight ocular light therapy units. An example is shown in U.S. Pat. No. 6,488,698 (Hyman). Such units, though smaller and less cumbersome than previously mentioned designs, are usually too large to be hand-held. Further, the Hyman device has no display or other means to convey information.

Another approach involves using light emitting diodes (LEDs) to try to make ocular light therapy portable devices. However, prior art LED ocular devices tend to be harsh to the eyes and create retinal after imaging. Moreover, prior art LED devices are of limited portability because of power consumption that requires access to an external power outlet or relatively large cumbersome batteries, rather than using a portable or built-in battery pack.

Some products have been made portable by developing wearable devices that bring the light source close enough to the subject's eyes to achieve effective high-intensity lux outputs. These units typically incorporate smaller, less intense lamps that can be battery powered. Examples are shown in U.S. Pat. No. 5,447,528 (Geraldo); U.S. Pat. No. 6,350,275 (Vreman et al.); and U.S. Pat. No. 6,053,936 (Koyama et al.). Such devices tend to flood the user's field of vision with light. This makes it difficult for the user to look past the bright light source to more dimly lit surfaces to accomplish daily tasks. This arrangement can cause eyestrain, headache and other discomforts.

Ocular light therapy devices are useful in treating a large variety of mood and sleep disorders and problems, including circadian rhythm adjustments, jet lag, seasonal affective disorder, general depression, sleep disorders, and shift-work disorders, post- and ante-partum depression, pre-menstrual syndrome, late luteal phase dysphoric disorder (LLPDD), bulimia and eating disorders, and chronic fatigue. Each disorder and problem tends to require a different type of light therapy that could vary in light intensity, period of treatment, duration of treatment, frequency of treatment and so forth. Moreover, individual physical constitutions and responses to light therapy tend to vary widely, requiring the need to tailor treatment to each individual.

SUMMARY

In one embodiment of the present disclosure, a light therapy apparatus is provided for delivering ocular light to a subject to treat a disorder that is responsive to ocular light therapy. The light therapy apparatus comprises a power supply, a hand-held light output device, wherein the light output device includes a plurality of light sources powered by the power supply, and a programmable data processor coupled to the power supply and the light output device for controlling light emissions from the hand-held light output device.

In another embodiment of the present disclosure, a hand-held light therapy device is provided for delivering ocular light to treat a disorder that is responsive to ocular light therapy. The light therapy device comprises a power supply, a light output device comprising a plurality of light sources powered by the power supply, and a programmable data processor coupled to the light output device for controlling light emissions from the light output device. The plurality of light sources provides a light output limited to substantially blue light having a wavelength range of approximately 435 nm to 500 nm.

In another embodiment of the present disclosure, a method of light therapy is provided wherein ocular light is provided to a subject to treat a disorder that is responsive to ocular light therapy. The method comprises delivering the ocular light to the eyes of a subject by a hand-held light output device powered by a power supply, and modifying the light emitted from the hand-held light output device using a programmable data processor coupled to the power supply and the light output device.

In yet another embodiment of the present disclosure, a light therapy method for delivering ocular light to treat a disorder that is responsive to ocular light therapy is provided. The method comprises delivering the ocular light to the eyes of a subject by a hand-held light output device powered by a power supply, and modifying the light emitted from the hand-held light output device using a programmable data processor coupled to the light output device. The hand-held light output device provides a light output limited to substantially blue light having a wavelength range of approximately 435 nm to 500 nm.

BRIEF DESCRIPTION OF DRAWINGS

FIG. 1A is a schematic diagram illustrating another exemplary light device of the present disclosure, according to one embodiment;

DETAILED DESCRIPTION

Introduction

Figure 1A:
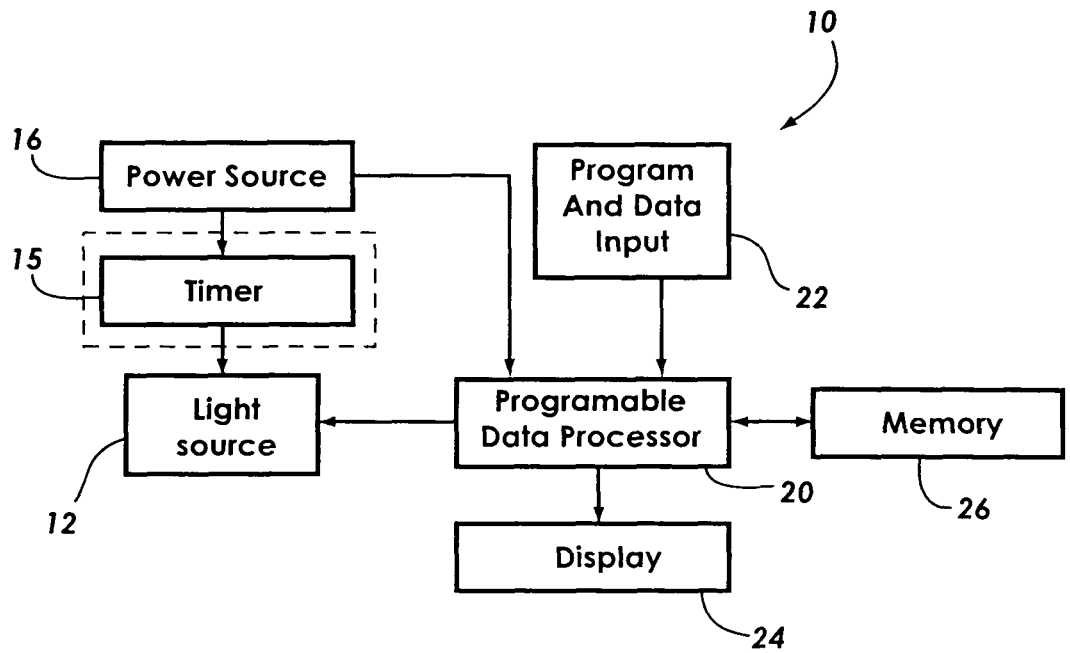
FIG. 1A is a schematic diagram illustrating an exemplary light device of the present disclosure, according to one embodiment.

The present invention involves a programmable ocular light therapy device and methods for using the device. The programmable ocular light therapy device can be equipped with program memory for storing different light therapy treatment programs for use by different individuals and/or for different types of treatment. The programmable ocular light therapy device can be configured to provide ocular light having substantially blue light, that is light having at least approximately forty percent (40%) of the light with wavelengths in the range of approximately 435 nm to 500 nm. In some embodiments, the light provided to the subject may comprise substantially solely blue light. In addition, the present invention provides for testing light therapy treatment programs to analyze the needs and responses of different individuals in order to individually tailor light therapy treatments.

In one embodiment, the programmable ocular light therapy device of the present disclosure delivers a full spectrum of light to the subject, while being fully portable. In another embodiment, the programmable ocular light therapy device delivers a spectrum of light emphasizing light in the blue range of the light spectrum. As used herein, the term "blue light" refers to light having wavelengths in the range of approximately 435-500 nanometers (nm). Blue light used for ocular light therapy purposes has been found to provide less glare, intensity and harshness to the subject's eyes. Further, blue light is more effective in suppressing melatonin to minimize the inducement of sleep.

In addition, the programmable ocular light therapy device of the present disclosure provides a process to make circadian rhythm adjustments in a subject's body (i.e., a human body) suffering from jet lag by selectively applying ocular light based on the direction and extent of travel experienced by the subject. The programmable ocular light therapy device of the present disclosure is also effective in treating other light-related problems, such as other circadian rhythm problems, seasonal affective disorders, some forms of depression, sleep disorders, and shift-work disorders, post-partum and ante-partum depression, pre-menstrual syndrome, late luteal phase dysphoric disorder (LLPDD), bulimia and eating disorders, and chronic fatigue.

The ocular light therapy devices of the present disclosure are much different from tissue light therapy devices that treat damaged muscles, tendons or skin. That type of light therapy device typically treats damaged tissue with infrared light radiation. The purpose is usually to provide heat to the damaged tissue, thereby increasing circulation to accelerate the healing process. Such light therapy devices are not concerned with providing light therapy to the eyes of a subject for treatment of circadian rhythm problems, seasonal affective disorders, depression, sleep disorders, and the like, as in the ocular light therapy devices of the present disclosure.

The programmable ocular light therapy devices of the present disclosure are not only portable, they are preferably hand-held devices. As used here, the term "portable" shall be broadly understood to mean being capable of being easily transferred to different locations. Thus, typically a unit the size of a briefcase or smaller might be termed to be portable, even though it must be connected to a wall outlet power source at each location. There is also a category of ocular light therapy devices referred to as "wearable," distinguished by being able to wear the device on the body, usually in close proximity to the eyes, such as on a visor. Wearable devices are further characterized by having a relatively low output, so that they are normally placed just a few inches from the eyes in order to be effective. As used herein, the term "hand-held" refers to ocular light therapy portable devices that are not wearable, that are capable of being powered by portable batteries, and that are relatively small—about 3 to 4 pounds or less and having dimensions in each direction of less than approximately 10 inches.

The programmable ocular light therapy devices of the present disclosure include programmable means for making changes and adjustments to various parameters of the light therapy treatment, including light intensity, light spectrum, the starting day and ending day for treatment, the time of day and length of each treatment, and the frequency of treatment times T the programmable light therapy device may include memory means for loading and storing multiple light treatment programs for different individuals and/or different types of treatments. Further, the programmable ocular light therapy devices may include test programming for quizzing each user to determine various parameters about the user and his or her needs, so as to individually tailor a light therapy program for each user.

Exemplary Housing Structures of Programmable Ocular Light Therapy Devices

Figure 1B:
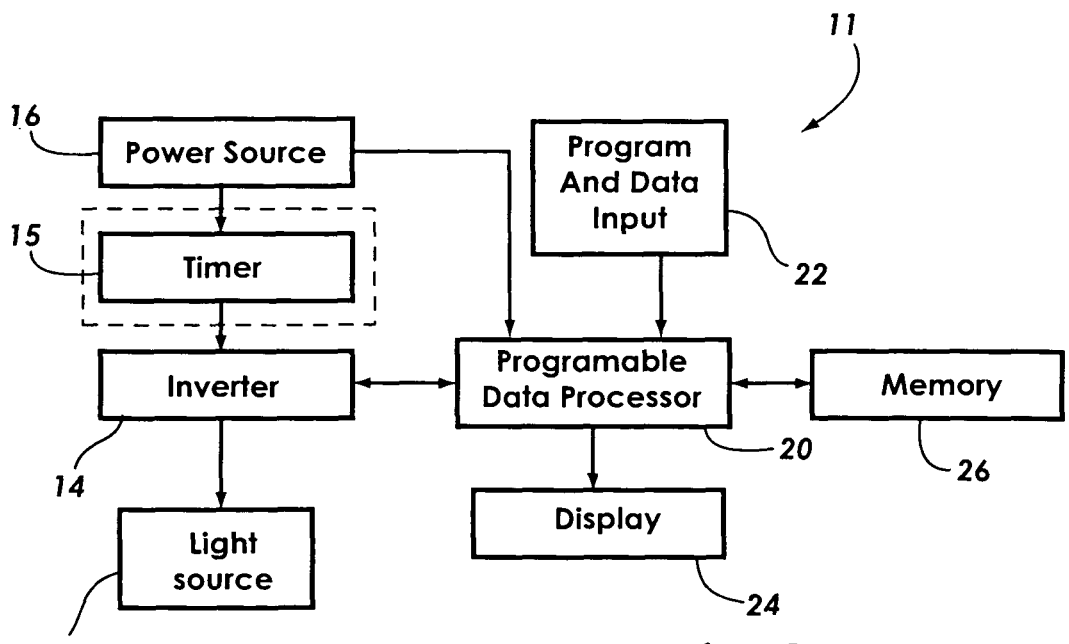

FIGS. 1A and 1B are generalized schematic diagrams showing two different embodiments of elements of a hand-held light therapy device 10, according to one embodiment of the present disclosure. The embodiment of FIG. 1A may be used in the event that a light source 12 comprises light emitting diodes (LEDs) or other similar sources. The embodiment of FIG. 1B may be used in the event a light source 13 comprises fluorescent lamps or other source that operates with an inverter 14.

Looking first at FIG. 1A, the light source 12 may be powered by a power supply 16, which may comprise a battery, rechargeable or not. Alternately, the power supply 16 may comprise an AC adaptor or transformer (not shown) connected to a standard power outlet. Power supply 16 may be rechargeable and connected to a recharger 18 that in turn may connect to a conventional AC power outlet. Power supply 16 also supplies power to a programmable data processor 20 that has two-way control and data communication with a memory 26. Although a programmable data processor 20 is shown in FIGS. 1A and 1B, in other embodiments, a non-programmable data processor may be used to control emissions of light from the light source 12, especially emissions of light within the blue light range, as described below.

Data is provided to programmable data processor 20 by program and data input device 22. Programmable data processor 20 processes input data according to internally stored programs to operate the light source 12. Programmable data processor 20 is connected to memory unit 26, which can store various light therapy treatment programs, analysis programs, parameters of the light source, timing data and other information that may be useful in customizing light therapy treatment for each individual and situation. Such programs may also be provided directly from an external source via the program and data input device 22.

Programmable data processor 20 also provides data output to a display 24 for displaying the time, the data being entering into the data processor 20, the status of the light therapy unit 10, the light therapy program being run, various light therapy programs that may be selected, and other information. The programmable data processor 20 may also include an internal timer in the form of software or firmware for operating the light source 12.

Alternately, a separate timer unit 15 may be connected between the power supply 16 and the light source 12, so that the device 10 may be manually actuated for a selected period of time. A dotted line around timer unit 15 indicates that it is optional and may be omitted from some embodiments. In embodiments not employing the timer 15, the power supply 16 and the data processor 20 may each be appropriately coupled to the light source 12.

Looking next at FIG. 1B, another light therapy device 11 similar to the light therapy device 10 is shown. In the device 11, however, the light source 13 may comprise a fluorescent light source or other type of light source configured to operate with an inverter 14, which may be positioned between the power supply 16 and the light source 13. Timer unit 15 is again optional.

Figure 2:
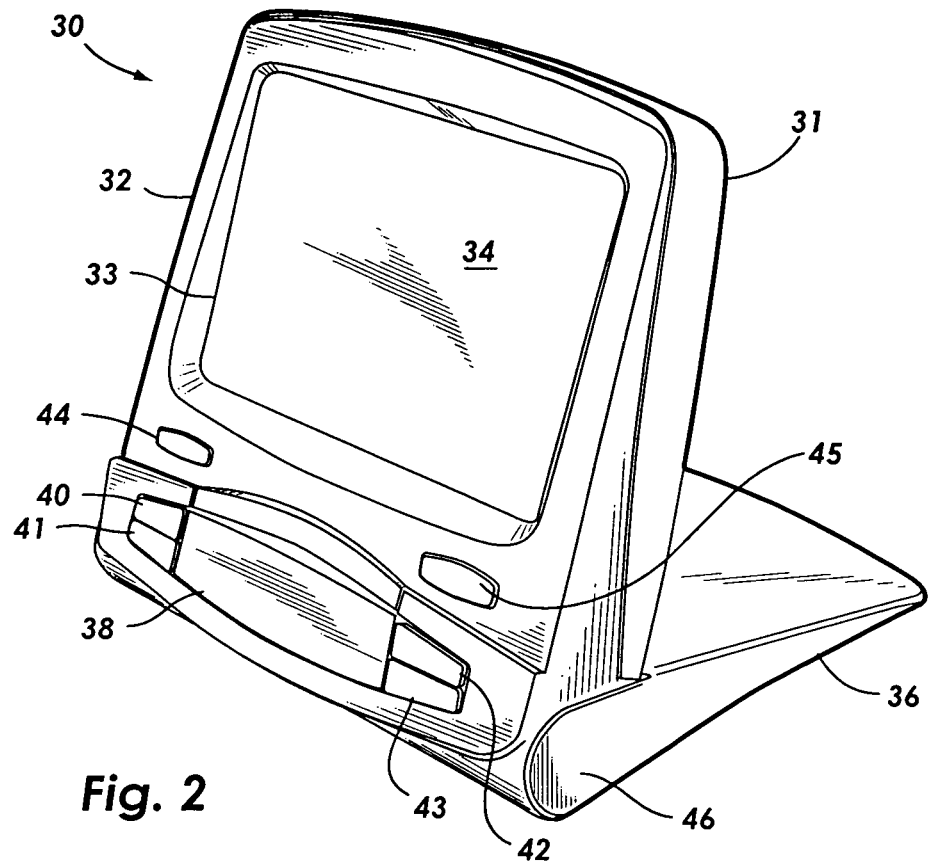
FIG. 2 is an open-cover perspective view of one implementation of the light device of FIG. 1A or FIG. 1B, according to one embodiment.
Figure 3:
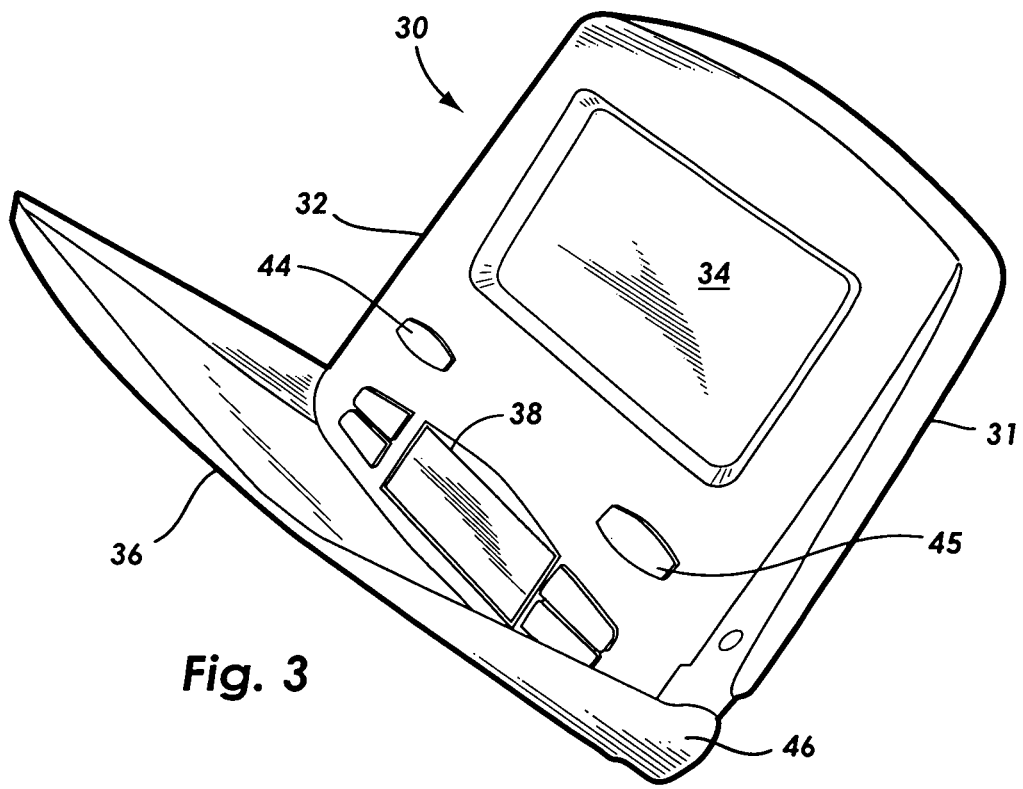
FIG. 3 is a partially closed-cover perspective view of the implementation of FIG. 2, according to one embodiment.
Figure 4:
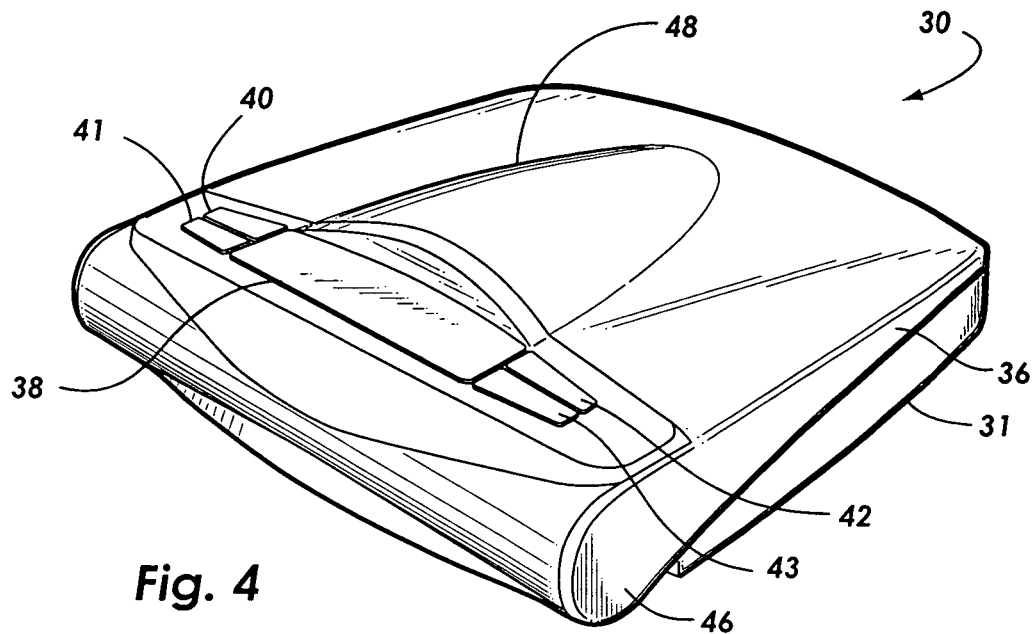
FIG. 4 is a closed-cover perspective view of the implementation of FIG. 2, according to one embodiment.

FIGS. 2, 3 and 4 show an exemplary housing structure with input and output elements, according to one implementation of a programmable hand-held ocular light therapy unit 30 (also referred to as the "unit 30" or the "device 30"). Unit 30 may be a battery powered, hand-held ocular light therapy device that utilizes a light source (not shown here) operated by a programmable processor (not shown here) having a memory for storing various programs and other data. The unit 30 may be placed in an open or closed orientation. In the open orientation, shown in FIG. 2, the light unit 30 has a base 36 for supporting the unit, so that light may be directed to a subject from a light source through a lens 34. A generally rectangular upper case 32 includes a recess 33 having the lens 34 therein. A light source (not shown), behind the lens 34, is disposed in the back portion 31 of case 32.

Upper case 32 rests in an upright position on a base 36, held in place by a protrusion 48 on the base (shown in FIG. 4). Below lens 34 is a display 38 for depicting messages and data during use. On either side of display 38 are data input buttons 40-43 for providing data to the unit 30, as will be discussed in detail hereafter. Between the display 38 and the lens 34 are two buttons 44 and 45, which function as on/off switches and to provide other main menu selections.

Looking now at FIGS. 3 and 4, when the unit 30 is not in use, it may be adjusted to a closed position. As shown in FIG. 3, base 36 is hinged at end 46 so that it rotates approximately 270 degrees about the upper case 32 that holds the light source (not shown) and lens 34. Accordingly, the base 36 is swiveled about the upper case 32, as shown in FIG. 3, so that base 36 covers and protects the light source lens 34, as shown in FIG. 4. With base 36 folded onto upper case 32, unit 30 is configured to sit flat on back portion 31 as shown in FIG. 4, with display 38 and buttons 40-43 on the top of the unit.

Thus, as shown in FIG. 4, base 36 becomes a cover to protect lens 34 and the light sources behind it, as well as buttons 44 and 45 shown in FIGS. 2 and 3. The closed position of the ocular light therapy device 30 shown in FIG. 4 not only protects the lens 34 and the light source (not shown), it also provides a slim, compact closed unit that may be hand-held and can easily be stored or transported. The closed hand-held ocular light therapy unit 30 shown in FIG. 4 may be about 6 inches tall, 6 inches wide, and about 2 inches deep, weighing about 8.4 ounces.

The device 30 shown in FIGS. 2 through 4 may employ a very thin (1/16 inch) lens 34 which may be textured and made of clear acrylic. The diffraction of the light passing through the texture of the lens 34 softens the high-intensity light and allows a more uniform treatment field. The acrylic properties of the lens 34 act to filter the ultraviolet rays so that the lens 34 will not yellow over time.

Ocular light therapy device 30 may be relatively small. In some embodiments, for example, the device 30 may be about six inches in length by five inches wide by two inches thick. Consequently, the device 30 is readily portable and may be used in travel, at the bedside and in many situations where larger units would be too intrusive.

Exemplary Light Sources for Programmable Ocular Light Therapy Devices

Figure 5:
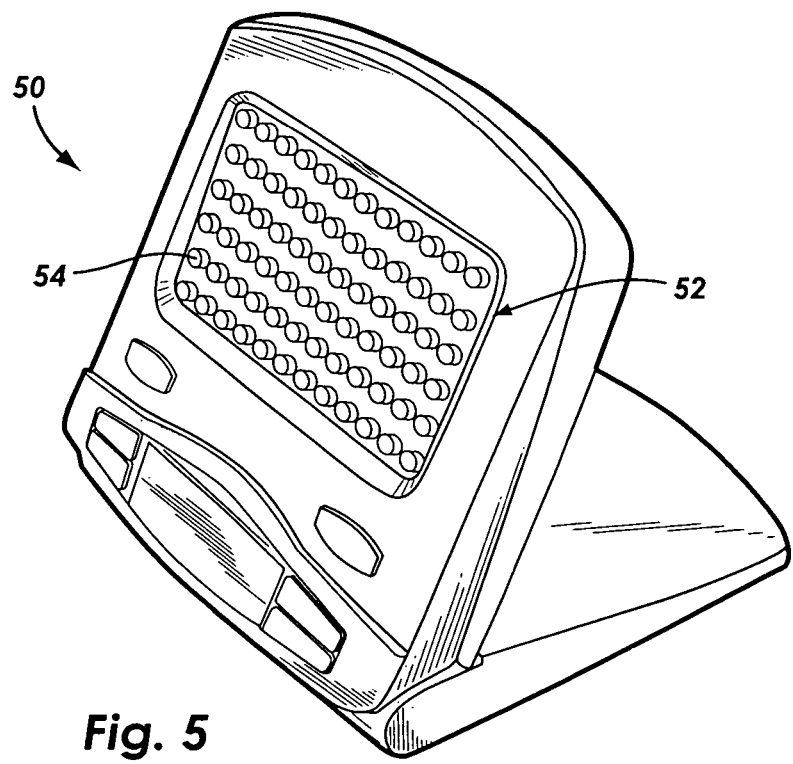
FIG. 5 is a perspective view of another implementation of the light device of FIG. 1A, according to one embodiment.
Figure 6:
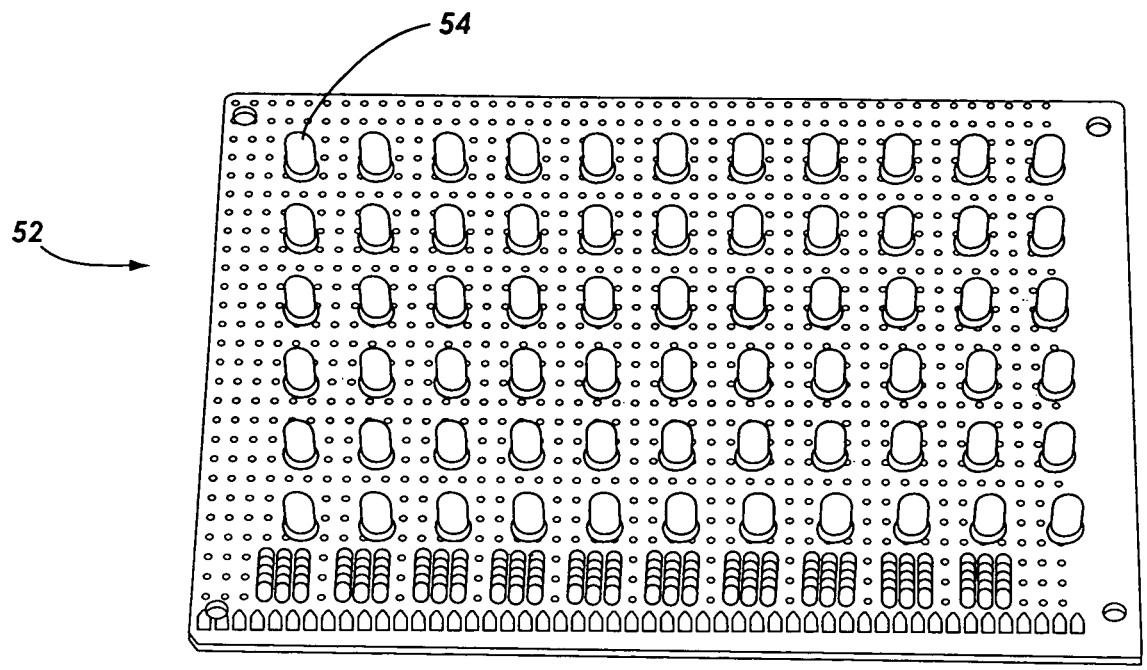
FIG. 6 is a perspective view of the LED matrix of the implementation of FIG. 5, according to one embodiment.

Referring now to FIGS. 5 and 6, a light emitting diode (LED) light therapy device 50 is shown. Lens 34, shown in FIGS. 2 and 3, has been removed to reveal a matrix 52 of LEDs 54, capable of being battery-powered. Matrix 52 may be composed of 66 LEDs 54 arranged in 6 rows and 11 columns. The LEDs may be five millimeter oval LEDs emitting a selected spectrum of visible light. For full-spectrum visible light, the light emission from light source matrix 52 may fall in an effective range of 1,000 lux to 2,000 lux at a distance range of approximately 6 to 12 inches from the matrix 52.

LEDs 54 may be configured to provide a full spectrum of light to a subject. However, many types of ocular light therapy devices have been found to be particularly effective when the LEDs 54 provide a spectrum of light having substantially "blue light," which refers to light having at least approximately forty percent (40%) blue light with wavelengths in the range of approximately 435 nm to 500 nm and generally having a distinctive, visible blue light color. Such blue light has been found to be particularly effective with a peak wavelength within the range of approximately 465 nm to 470 nm and a half-peak bandwidth of plus or minus approximately 30 nm. Light sources that are configured to emit concentrated blue-colored light have been found to provide excellent suppression of melatonin, to minimize the inducement of sleep. Accordingly, LEDs 54 may be configured to emit substantially solely blue light to a subject. In some embodiments, the LEDs 54 are configured to emit light comprising at least approximately fifty percent (50%) blue light with wavelengths in the range of approximately 435 nm to 500 nm and generally having a distinctive, visible blue light color.

Blue-colored light LEDs 54 have been found to be effective at lower power levels and/or greater distances than full spectrum light. For example, blue light therapy may provide useful treatment at distances of 15 to 30 inches between the subject and the light source, with an especially effective distance range being about 20 to 22 inches. In one embodiment, at a distance of 20 inches, effective blue light therapy is provided at only about 400 lux, or about $2.4\times10^{-4}$ watts/cm$^2$.

The blue light provided for therapy according to the present disclosure may be produced directly by light sources that provide light in the blue light wavelength range. Alternately, or supplementing such light, a light therapy device according to the present disclosure may utilize a lens or other device that filters white light or light in other wavelengths to provide substantially blue light to the subject.

Figure 7:
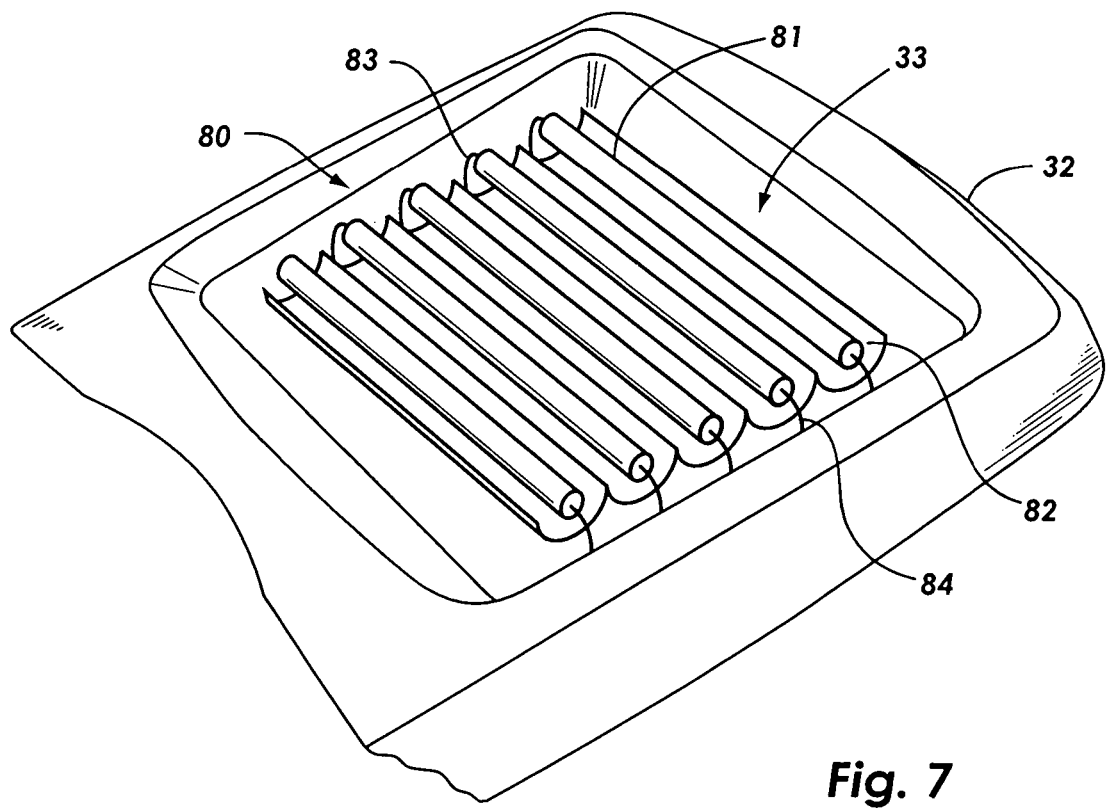
FIG. 7 is a partial perspective view of an implementation of the light device of FIG. 1B in which a fluorescent light device is used, according to one embodiment.
Figure 8:
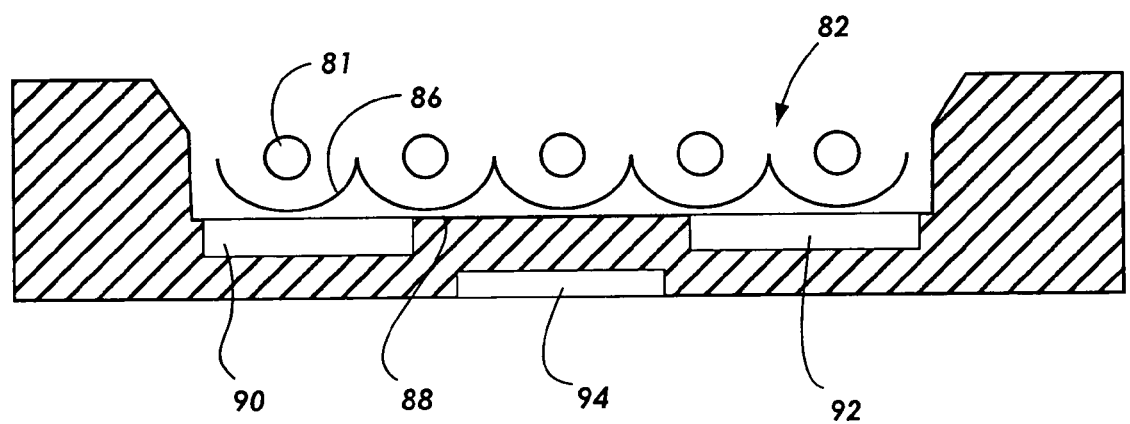
FIG. 8 is a side view of the implementation of FIG. 7, according to one embodiment.

Another implementation of the present invention is shown in FIGS. 7 and 8. A light source 80 shown therein may include a unique type of fluorescent light source referred to as cold cathode fluorescent lamps (CCFL tubes). CCFL tubes are usually low pressure lamps, possibly using mercury vapor, and having a very small diameter (for example, 2 to 3 mm) and short length (for example, 50 to 700 mm).

CCFL tubes have been used to provide background lighting for laptop computers and to provide light for scanning and copying, because they provide an even distribution of light and can produce full-spectrum coloring and/or single-out specific wavelengths. See, e.g., "A Cold Cathode Fluorescent Lamp (CCFL) Controller Used in Magnetic Transformer Application," by Weiyun (Sophie) Chen, an article located on the internet at a web page having the address of http://www-.chipcenter.com/analog/c070.htm (accessed Jun. 6, 2003). Another application of CCFL tubes is shown in U.S. Pat. No. 6,454,789 (Chen) where light is provided via fiber optics to treat tumors within a patient's body.

CCFL tubes are small and portable, and provide high efficiency in light output. CCFL tubes may provide a substantially full spectrum of light. However, similar to the LED embodiment mentioned in connection with FIGS. 5 and 6, the CCFL tubes are very effective by providing light that is limited to substantially blue light in the range of 435 nm to 500 nm wavelengths. Such blue light has been found to be particularly effective with a peak wavelength of 465 nm to 470 nm and a half-peak bandwidth of plus or minus approximately 30 nm.

Looking at FIG. 7, light source 80 is shown in detail. Six CCFL tubes 81 are placed in a generally parallel position relative to each other in recess 33 of case 32. A generally parabolic reflector 82 is positioned behind each of tubes 81 for directing light toward the front of the device 30 in which light source 80 is implemented. Each tube 81 has electrical connections 83 and 84 extending from each end of the tube 81 to connect to an inverter 90 (shown in FIG. 8).

FIG. 8 shows the light source 80 from a side view. Each of tubes 81 lies within the focal point of a parabolic portion 86 of reflector 82. Reflector 82 rests on a circuit board 88 to which the tubes 81 and reflector 82 are attached. On the underside of circuit board 88 is an inverter 90 and processor 92, corresponding to inverter 14 and processor 20 in FIG. 1. Power supply 94 may be disposed inside of case 32.

The light therapy unit 30 may use cold cathode fluorescent technology for the treatment of light related problems, such as circadian rhythm problems and mood and sleep disorders. The light therapy unit 30 described herein may provide long life (about 20,000 hours), substantially full-spectrum color and high output over specific wavelengths, such as blue light wavelengths, while minimizing the presence of ultraviolet wavelengths. The device also may have a high CRI (Color Rendition Index), which is a measure of the trueness of color reflected when the light is exposed to a given color. In addition, the CCFL tubes 81 of the device 30 may include an electrical connection lead 83 or 84 on each end.

The CCFL tubes 81 may have a very small diameter, about the size of a plastic ink cylinder of a small writing pen. For example, the CCFL tubes 81 may have a diameter of 2.2 mm and a length of 140 mm. The lamp voltage may be 340 volts with a wattage of 1.7 watts at 5 mA rms and a tube current of 6 milliamps. The inverter 90 may have a strike voltage of 730 volts and a sustain voltage in the range of 325-450 volts. The inverter frequency can be 60 kilohertz. Ramping and dimming may be done through pulse width modulation (PWM) of the CCLF current using the data processor. This PWM frequency is superimposed on the 60 khz current frequency, and averages 120 hz. By varying the duty cycle, the CCFLs can be dimmed by turning the current on and off at a sufficient rate to prevent the excitation of the lamp to decay, yet reduce the emissions.

Contrary to most uses of CCFL tubes, the high-intensity inverter 90 of the light therapy device 30 may be designed to run multiple CCFL tubes 81. This allows for fewer electronic components and thus lighter weight and smaller overall size of the unit. The efficiencies of CCFL technology allow the device 30 to be power supply-powered. The device 30 may be designed to run on a multi-current wall transformer 120 volts or 240 volts, plus or minus 20%. The device 30 may also contain rechargeable batteries with a capacity to allow multiple therapy sessions.

The parabolic reflector unit 86 may be made of aluminum or other material which is approximately 90% reflective or greater. The reflector material is bent in a parabolic shape that insures that the light emitted from the tubes 81 is reflected forward to the user.

It should be understood that the light therapy unit 30 shown above includes specific light source implementations of the generalized light therapy device 10 shown in FIG. 1. Both of the exemplary light therapy devices 30 and 50 described herein may be made to be powered by a conventional internal or external power supply pack. However, they may also be powered by an AC adaptor using standard wall-socket power.

Exemplary Functional Operations of Programmable Ocular Light Therapy Devices

Referring back to FIGS. 1-4, the ocular light therapy devices of the present disclosure may be programmed to provide a variety of functions by the data processor 20. Data buttons 40-45 may be manipulated by a user to provide data and/or parameters to the data processor 20 in order to vary the timing or intensity of light emissions, or to set up one or more personalized programs that may be actuated at will or by a timer.

Thus, for example, the data processor 20 of the device 10 may include software or firmware with an ability to vary the intensity of the light source 12, including an ability to dim down and ramp up the intensity of the light output from the light source 12. Alternately, for fluorescent light sources, a dimming/ramping function may be built into the inverter 14, as described above. The dimming function enables a dusk simulation to aid in falling asleep, and the ramping function allows a dawn simulation for natural waking. Other embodiments may include a separate conventional dimmer device (not shown) connected between the power supply 16 and the light source 12 or 13.

Buttons 40-45 may be used to provide plus (increase) and minus (decrease) functions, such as to adjust the amount of light that the light source 12 provides by changing the intensity of the light source 12. By pushing a button designated as plus, the intensity will be increased so that the light source 12 is brighter. A button designated as minus causes the intensity of the light source 12 to decrease. Thus buttons 40-45 may be connected to the inverter 14 or associated dimmer (not shown), as described above with respect to FIG. 1, to enable a user to adjust the light source intensity to a level that is comfortable for that user.

Looking again at FIG. 1, the timer 15 or the timing function in processor 20 may also be controlled by manipulating buttons 40-45, shown in FIGS. 2-4. A user may select the amount of time in minutes that a light source (12; FIG. 1) is to be actuated, thereby eliminating any need to watch the clock. The time will count down and automatically turn off the light source (12; FIG. 1) when the designated time has elapsed. A clock may be built into the processor 20 and connected to display the time on the display unit 24.

Another device that may be controlled by data buttons 40-45 is the display 24. Any conventional light display means, such as LCDs or LEDs may be utilized in display 24. The display may show various information, including but not limited to current time, timer, current light intensity, current program and battery power remaining. The data buttons 40-45 may also control a built-in alarm device or alarm clock (not shown) to alert the user at various times, such as a wake-up time or a time for therapy treatment to begin or end. The data buttons 40-45 may be used to adjust and modify the operation of the alarm device or of an associated alarm clock. A built-in calendar may also be accessed by the data buttons 40-45 to arrange for multiple light therapy sessions on selected days.

Sample Programs Utilized by the Programmable Ocular Light Therapy Devices

In addition to the foregoing functions, buttons 40-45, shown in FIGS. 2-4, may be manipulated to provide data and parameters to the processor 20, in order to set up one or more personalized programs that may be actuated at will or by the timer 15, shown in FIG. 1, or by an internal timer in processor 20.

Figure 9:
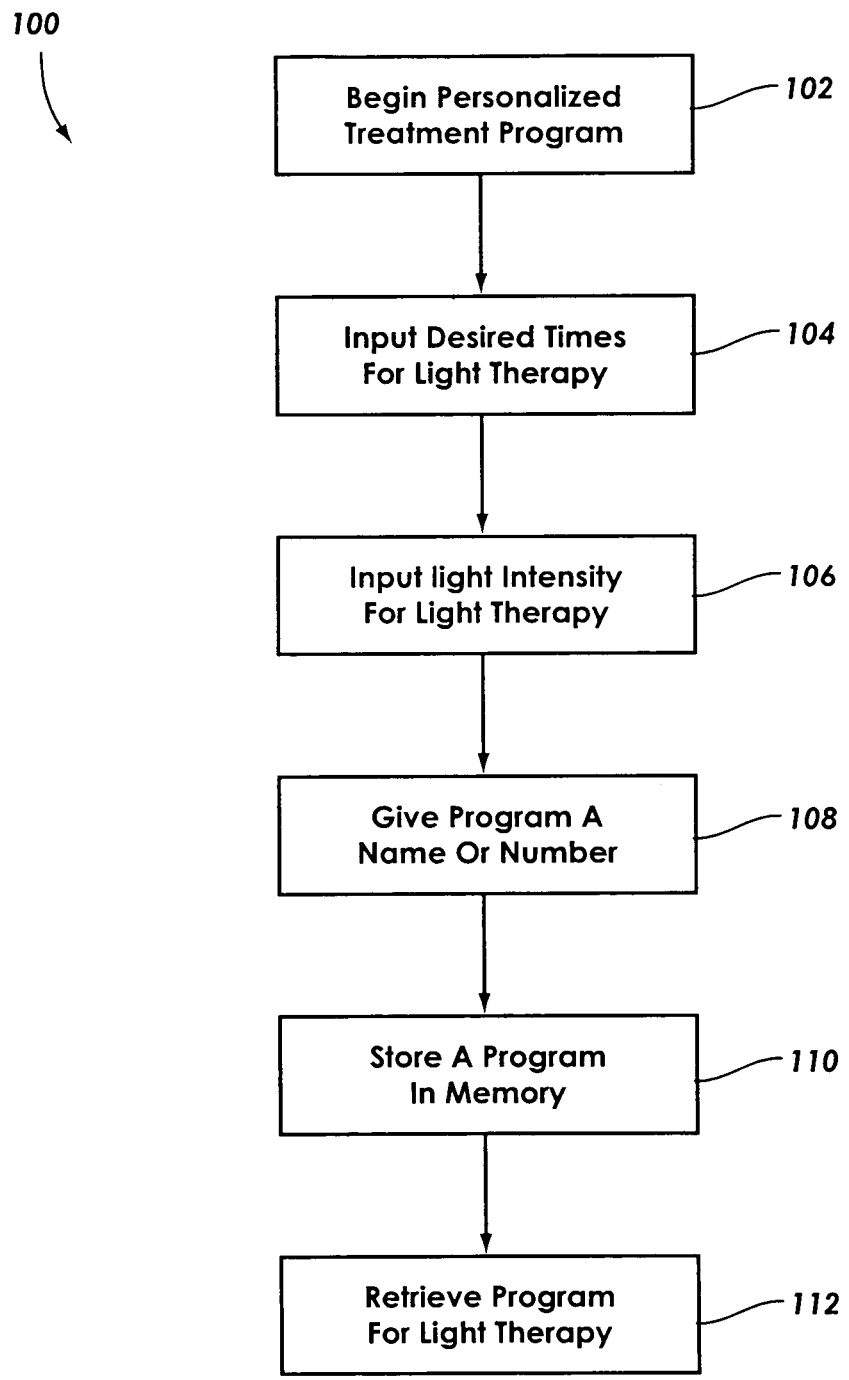
FIG. 9 is a flow diagram showing an implementation of a light delivery method, according to one embodiment.

FIG. 9 shows an exemplary process 100 for creating a personalized treatment program, beginning at step 102. Each user is different, and the buttons 40-45 may be used to help each individual create and run his/her own individual program. At step 104, a user may input a desired time for light therapy to start and stop. Then at step 106, the user may input the desired light intensity for the light therapy, again using buttons 40-45. The light intensity may be programmed to provide different intensities of light at different times during therapy. For example, the light intensity may gradually increase to simulate a sunrise at dawn. Alternately, the light intensity may gradually decrease to simulate a sunset at dusk. Next, at step 108, the user may give the program a name, number, or other identifier. At step 110, the program is stored in the memory 26.

Thereafter, other users may similarly set up their own individualized therapy program and store it in the memory 26. When a user is ready to use the ocular light therapy unit 10 for his/her therapy, at step 112, the data buttons 40-45 may be used to enter the pre-assigned identifier of the program, which may then be actuated as desired. Any of the stored programs may be recalled and actuated as directed, using buttons 40-45 of FIGS. 2-4. The programs may also be set up to be automatically actuated at designated times by the timer 15 shown in FIG. 1 or by an internal timer in processor 20. The built-in calendar may also be used to trigger operations of the light therapy program over several days, weeks, months or even years, as desired.

Figure 10:
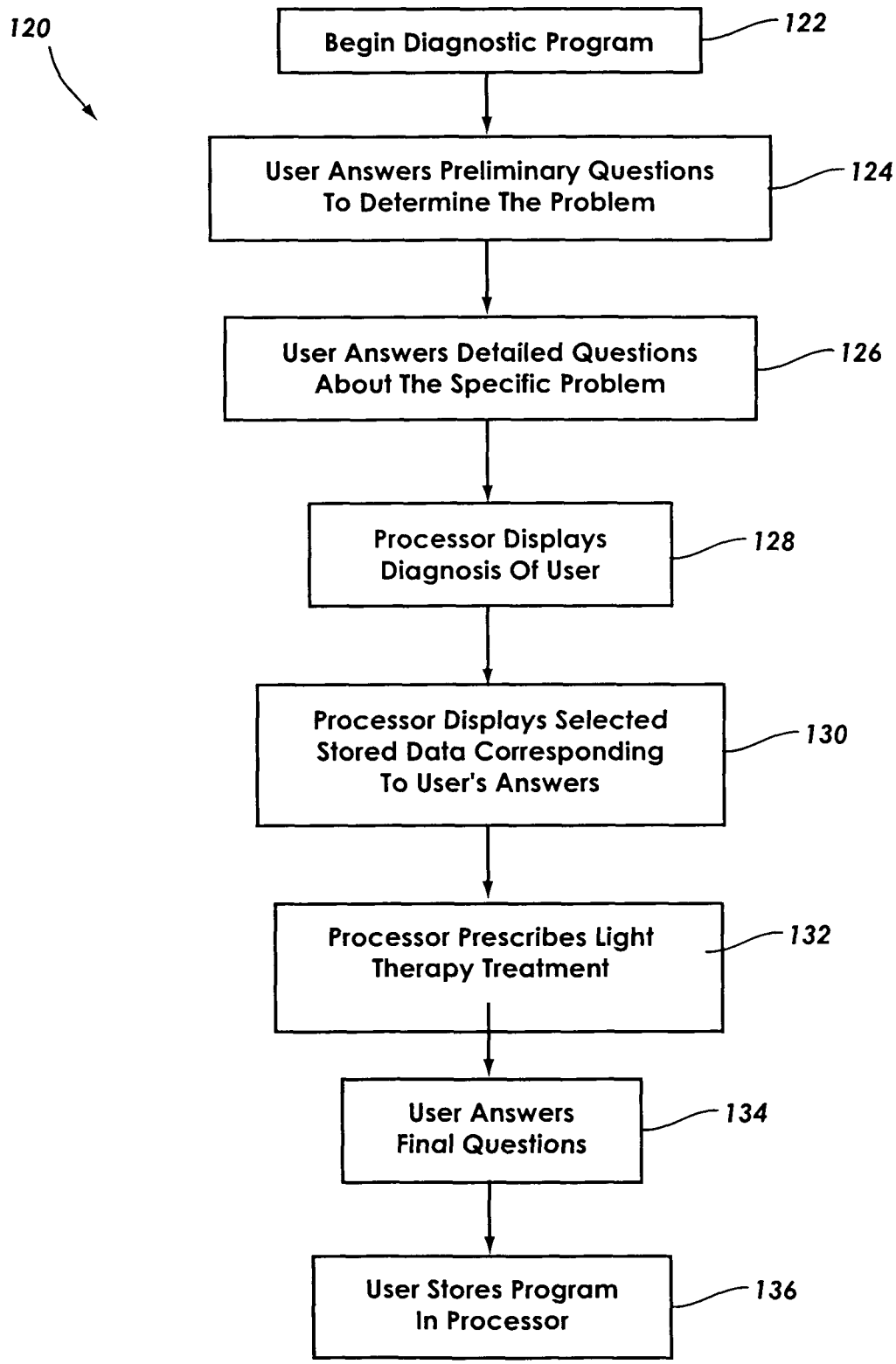
FIG. 10 is a flow diagram showing another implementation of a light therapy method, according to one embodiment.

Referring now to FIG. 10, the processor 20 may be configured to run a diagnostic program 120 for diagnosing a condition of a user for the purpose of generating and recommending a light therapy program. The program 120 begins at step 122 by a user inputting data on buttons 40-45 to initiate the diagnostic program 120. At step 124, a user is asked a series of questions to determine his or her condition, status and health. For example, the user may be asked what condition he/she has that may require light therapy. The user's answers may be entered via data buttons 40-45. For example, the user may indicate that he or she is suffering from seasonal affective disorder (SAD).

The processor 20 may then ask follow-up questions, at step 126, to determine the extent of SAD symptoms that the user has, how long he or she has had them, how severe the symptoms are, and other such questions to obtain more details. If the user is using light therapy to treat jet lag, the follow-up details might be to determine the user's travel plans. If the user is undergoing light therapy for a sleep disorder, the detail questions might relate to sleep patterns, wake patterns, and so forth. Again, the user may enter answers to the detailed questions using buttons 40-45 of FIGS. 2-4.

The processor 20 uses the answers to determine and display a diagnosis, at step 128. When preliminary testing has been completed, the processor 20 may select internally stored data that is relevant to the diagnosis of the user and display it, at step 130. In addition, the processor 20 may use the diagnosis to prescribe a personalized light therapy program, based on answers given by the user, at step 132. For example, the program might indicate what time to use light therapy and for how long each time. It may also recommend the light intensity and the number of days of treatment. This information may be displayed to the user, who will then determine whether to activate a suggested program, store the program for future use or discard the program. Additional questions may be asked and answered, at step 134, regarding whether to sound a reminder alarm at treatment time, whether to name the program for repeat use, and so forth.

The user may take the same test at different times to determine whether the light therapy for his/her problem needs to be modified, in view of changing circumstances. For example, each instance of airlines travel may lead to a different diagnosis. On the other hand, a traveler may take the same routine trips. In that case, the traveler may name the treatment of the trip being taken and store the program, at step 136, so it can be used over again without undergoing the same diagnosis, such as "Steve SLC-NY." Likewise, if a subject suffers from SAD each winter, he may simply store a program called "Steve-SAD" for use at the appropriate time each year.

In a variation to the diagnosis program shown in FIG. 10, the user may undergo automated diagnosis using a website on the internet by similar steps to those shown in FIG. 10. The user may then be presented with a diagnosis and recommended light therapy treatment from the same or a different website. The website may provide data and parameters for a desired light therapy program, which the user inputs to the processor 20 via the data buttons 40-45. This information is used to select a stored program in processor 20 or memory 26, or is stored in memory 26 for future use. Alternatively, the user may take a diagnosis test on a computer using a software program, or using a cellular telephone, a PDA, or other communications device.

In another variation to the diagnosis program shown in FIG. 10, for programs that a user will utilize repeatedly, he/she may choose to store the programs in a computer or other remote memory. In that case, the programs may be later retrieved and downloaded from a computer, the Internet, or other device using a cable, a wireless system, or other suitable transmission medium and protocol.

In yet another variation to the programs shown in FIGS. 9 and 10, an ocular light therapy device may utilize a remote control device (not shown) to carry out any of a number of functions, including but not limited to turning the light source 12 on and off, selecting a treatment, adjusting the intensity, setting the timer, setting a wake time, and so forth. The remote device may also include a display that would show the same information shown on display 24 in FIG. 1 or display 38 in FIGS. 2 and 3.

The processor 20 shown in FIG. 1 may include an atomic clock and a jet-lag calculator to help travelers to change their sleep patterns and circadian rhythms when they travel. The atomic clock may monitor time across time zones and display the time at the current location. The jet-lag calculator may advise a user, when traveling, about the times to use the device and the amount of light usage. The data may also advise the user when to avoid outdoor light.

Figure 11:
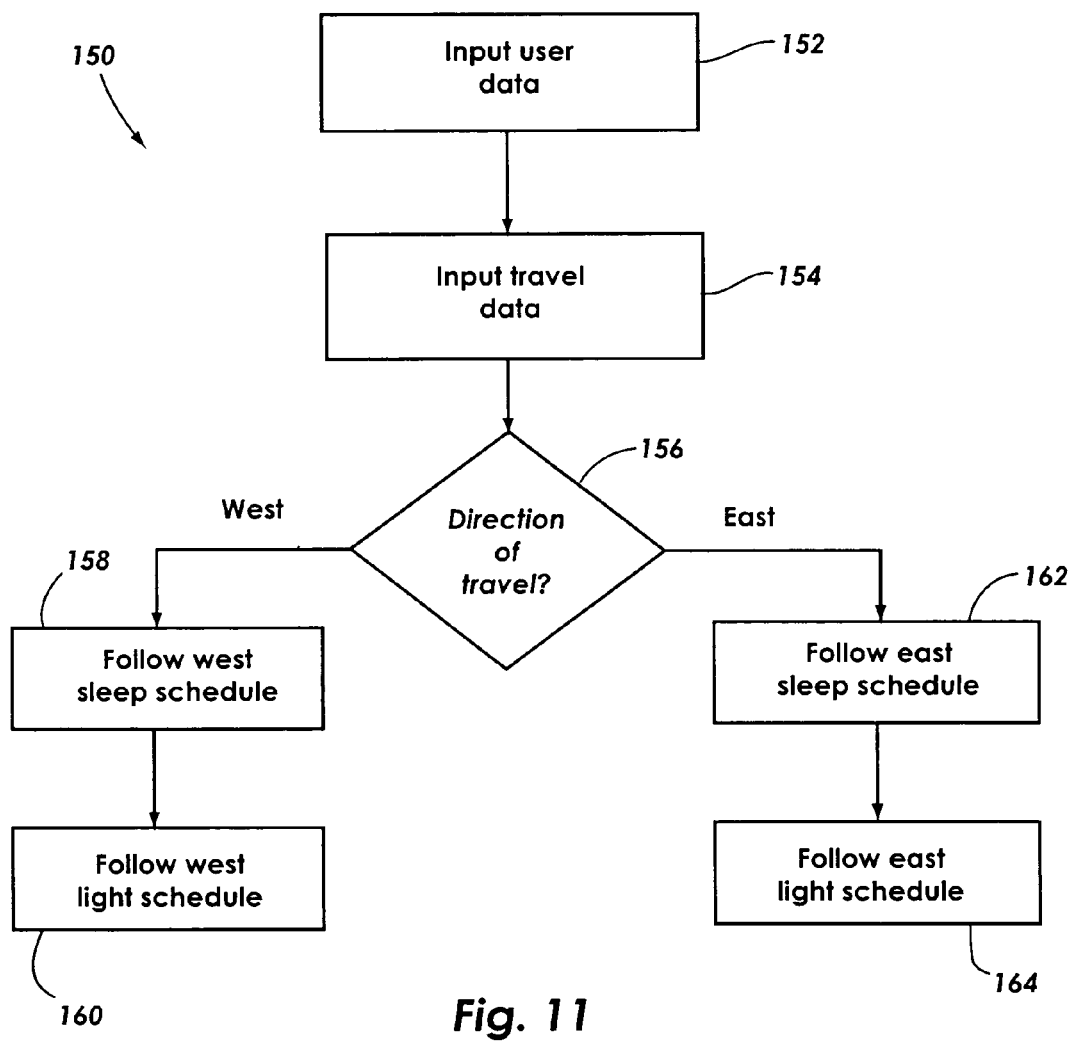
FIG. 11 is a flow diagram showing yet another implementation of a light delivery method, according to one embodiment.

Looking now at FIG. 11, a flow diagram is shown illustrating a process 150 for providing light therapy to treat jet lag, using the processor 20 shown in FIG. 1. The processor 20 may employ an algorithm that accepts data input from a user. This data may include user data inputs 152 and travel data 154. The software utilized by the processor 20 could be embedded in the processor 20, accessed in memory 26, or downloaded by processor 20 from the internet, mobile telephone, PDA, computer or other external source.

Examples of data that may be input to the processor 20 can include the departure airport, arrival airport, natural sleep time and natural wake time. It is known that, in order to achieve the best adjustments in the circadian rhythm, light should be administered relative to the time when the core body temperature is at a minimum. It is also known that, typically, the core body temperature minimum occurs about two hours before the natural wake up time.

The time to expose a subject to light also depends on whether the subject is traveling east-bound or west-bound. If the subject is eastbound, the circadian rhythm adjustment is best made if light is administered after the time when the core body temperature is at a minimum. If the subject is westbound, the circadian rhythm adjustment is best made if light is administered before the time when the core body temperature is at a minimum.

Accordingly, the data to the processor 20 may include the number of time zones traveled, the direction of travel, and the core-body temperature of the traveler. The process 150 then determines at step 156 whether the traveler is headed east or west. The process 150 then uses either west-bound sleep and light schedules 158 and 160 or east-bound sleep and light schedules 162 and 164 to calculate a sleep/wake, light/dark regimen and instructions to facilitate the avoidance of jet lag problems. The digital display 24 of the device 10 can provide function and text displays to provide the results of the jet-lag calculations.

The data input regarding a subject may also include data regarding whether the subject is "sleep delayed" or "sleep advanced." A sleep delayed subject tends to stay up later and have a more difficult time awakening in the morning, whereas a sleep advanced subject tends to want to go to bed earlier and get up earlier. This data could require separate west-bound and east-bound schedules, depending whether the subject was sleep delayed or sleep advanced.

In one implementation of a light therapy method, the user input is the natural wake up time and the natural fall-asleep time. From this data the processor 20 may calculate the time at which the core body temperature is expected to be at a minimum. The user then inputs the departure airport and the arrival airport. The processor 20 may calculate the number of time zones to travel and the direction of travel. The process then displays the regimen to follow for each day in order to administer the proper amount of high intensity light for a desired period of time and at the right time. Suggestions may also be given regarding when to go to bed and when to wake up.

The following is an example of implementing the above procedure:
User Inputs:
Natural wake time=7:00 am
Natural fall-asleep time=11:00 pm
Processor Calculates:
User Inputs:
Departure Airport=Washington, D.C.
Arrival Airport=Paris, France
Processor Calculates:
Number of time zones to travel=6
Direction of travel=East
Number of days needed to shift sleep pattern=3
Processor Displays:
First day regimen=6 am (East coast time) receive 10,000 lux light exposure, 0.5 hrs. (day before departure).
Second day regimen=4 am (East coast time) receive 10,000 lux light exposure, 0.5 hrs. (departure day).
Third day regimen=8 am (Paris time) 10,000 lux light exposure, 0.5 hrs. (day of arrival)

In addition, the present light therapy devices may take into account the time when the traveler decides to start making adjustments to the circadian rhythm relative to the time that he begins traveling. For example, a traveler may prefer or be unable to start adjusting the circadian rhythm until arriving at his destination. In such case, the regimen required for making the circadian rhythm adjustment would be considerably different than if the adjust began before the day of travel. The processor 20 in the current device can take the selected start time into account and make the appropriate adjustments in the calculations.

The foregoing discussion deals, by example only, with jet lag travel problems requiring circadian rhythm adjustments. Other types of circadian rhythm disorders or problems may also be effectively treated with the current light therapy device using appropriate data inputs and calculations. Further, the light therapy device may also be useful in treating other types of mood and sleep disorders that are usually responsive to light therapy, including but not limited to seasonal affective disorder, general depression, sleep disorders, and shift-work disorders, post- and ante-partum depression, pre-menstrual syndrome, late luteal phase dysphoric disorder (LLPDD), bulimia and eating disorders, and chronic fatigue.

Although the above embodiments are representative of the present invention, other embodiments will be apparent to those skilled in the art from a consideration of this specification and the appended claims, or from a practice of the embodiments of the disclosed invention. It is intended that the specification and embodiments therein be considered as exemplary only, with the present invention being defined by the claims and their equivalents.

What is claimed is:

1. A light therapy apparatus for delivering ocular light to an eye of a subject to treat a disorder that is responsive to ocular light therapy, the light therapy apparatus comprising:
   a power supply;
   a hand-held light output device configured to have outside dimensions in each direction of less than 10 inches and comprising a plurality of light emitting diode (LED) devices coupled to the power supply to power the plurality of LED devices; and
   a programmable data processor coupled to the power supply and the hand-held light output device and configured to control light emissions from the hand-held light output device to emit a selected spectrum of visible light with a light emission in an effective range of 1,000 lux to 2,000 lux at a distance of 6 to 12 inches.

2. The light therapy apparatus of claim 1, wherein the programmable data processor includes software or firmware that configures the programmable data processor to vary the intensity of the light output.

3. The light therapy apparatus of claim 2, wherein the software or firmware configures the programmable data processor to provide a ramping function to progressively increase light intensity emitted from the hand-held light output device to simulate a sunrise at dawn or to progressively dim light intensity emitted from the hand-held light output device to simulate a sunset at dusk.

4. The light therapy apparatus of claim 1, wherein the programmable data processor includes a timing function to control the amount of time that the hand-held light output device provides light to the subject.

5. The light therapy apparatus of claim 1, wherein the hand-held light output device provides light having at least forty percent blue light with wavelengths in a range of approximately 435 nm to 500 nm.

6. The light therapy apparatus of claim 5, wherein the hand-held light output device provides light having a peak wavelength of 465 nm to 470 nm with a half-peak bandwidth of as low as approximately 435 nm and as high as approximately 500 nm.

7. The light therapy apparatus of claim 5, further comprising a lens in the hand-held light output device configured to provide the blue light.

8. The light therapy apparatus of claim 1, wherein the hand-held light output device is configured to provide light limited to substantially solely blue light with wavelengths in a range of 435 nm to 500 nm.

9. The light therapy apparatus of claim 1, wherein the power source comprises a portable battery.

10. The light therapy apparatus of claim 1, wherein the power source comprises an adaptor or transformer.

11. The light therapy apparatus of claim 1, further comprising a display coupled to the programmable data processor and configured to display data and messages from the processor.

12. The light therapy apparatus of claim 1, further comprising a data input device coupled to the programmable data processor to provide data to the processor.

13. The light therapy apparatus of claim 12, further comprising a memory coupled to the programmable data processor to store data relating to the operation of the light output device.

14. The light therapy apparatus of claim 13, wherein the memory stores a light therapy program for controlling operation of the programmable data processor.

15. The light therapy apparatus of claim 14, wherein the data input device is configured to receive input to control the programmable data processor to control the hand-held light output device.

16. The light therapy apparatus of claim 14, wherein the light therapy program includes a diagnosis program configured to develop a personalized light therapy program based on data input to the programmable data processor or the memory by way of the data input device.

17. The light therapy apparatus of claim 1, wherein the plurality of LED devices are arranged in a matrix to direct therapeutic light to the eye of the subject.

18. A light therapy device for delivering ocular light to treat a disorder that is responsive to ocular light therapy, comprising:
a power supply;
a hand-held light output device having outside dimensions in each direction of less than 10 inches and coupled to the power supply and comprising a plurality of light emitting diode (LED) devices powered by the power supply; and
a data processor coupled to the hand-held light output device and configured to control light emissions from the plurality of LED devices to emit a selected spectrum of visible light with a light emission in an effective range of 1,000 lux to 2,000 lux at a distance of 6 to 12 inches.

19. The light therapy device of claim 18, further comprising a lens in the hand-held light output device configured to provide the blue light.

20. The light therapy device of claim 18, wherein the hand-held light output device is configured to provide light limited to substantially solely blue light with wavelengths in a range of approximately 435 nm to 500 nm.

21. The light therapy device of claim 18, wherein the power source comprises a portable battery.

22. The light therapy device of claim 18, wherein the power source comprises an adaptor or transformer.

23. The light therapy device of claim 18, wherein the hand-held light output has a visible blue color.

24. The light therapy device of claim 18, wherein the light output has a peak output wavelength of 465 nm to 470 nm, with a half-peak bandwidth of at least approximately 435 nm and at most approximately 500 nm.

25. The light therapy device of claim 18, wherein the data processor is configured to vary the intensity of the light output.

26. The light therapy device of claim 25, wherein the data processor is configured to provide a ramping function to progressively increase the light output to simulate a sunrise at dawn or to progressively dim the light output to simulate a sunset at dusk.

27. The light therapy device of claim 18, further comprising a memory coupled to the data processor, the memory having a light therapy program stored therein, and a data input device for the subject to provide data to the data processor.

* * * * *